United States Patent [19]

White

[11] 4,295,362

[45] Oct. 20, 1981

[54] PENTAERYTHRITOL IN DRY DEVELOPERS

[75] Inventor: Michael L. White, Lake in the Hills, Ill.

[73] Assignee: Magnaflux Corporation, Chicago, Ill.

[21] Appl. No.: 123,683

[22] Filed: Feb. 22, 1980

[51] Int. Cl.³ .................... C09K 3/00; G01N 19/08; G01N 33/00

[52] U.S. Cl. .................... 73/104; 252/301.19; 252/408; 23/230 R

[58] Field of Search ............ 73/104; 252/408, 301.19; 23/230 R

[56] References Cited

U.S. PATENT DOCUMENTS

| | | | |
|---|---|---|---|
| 2,676,487 | 4/1954 | Clarke | 252/408 |
| 2,764,556 | 9/1956 | Sockman et al. | 252/408 |
| 2,806,959 | 9/1957 | De Forest et al. | 252/408 |
| 3,433,062 | 3/1969 | Molina | 252/408 |
| 3,456,110 | 7/1969 | Diperstein | 252/408 |
| 3,538,016 | 11/1970 | Borucki | 252/408 |
| 3,560,399 | 2/1971 | Irsak | 252/408 |
| 3,561,262 | 2/1971 | Borucki et al. | 252/408 |
| 3,642,655 | 2/1972 | Borucki | 252/408 |
| 3,803,051 | 4/1974 | Molina | 252/408 |
| 4,000,422 | 12/1976 | Kuzmima et al. | 252/408 |

OTHER PUBLICATIONS

Eastman Organic Chemicals, Catalog, No. 47, Eastman Kodak Co., Rochester, N.Y., p. 170, (1974).

Primary Examiner—Teddy S. Gron
Attorney, Agent, or Firm—Hill, Van Santen, Steadman, Chiara & Simpson

[57] ABSTRACT

A method and composition for detecting surface flaws in workpieces by means of the penetrant inspection process, the invention being concerned with an improved dry developer composition for use in such process, the developer containing substantial amounts of pentaerythritol, usually in combination with a finely divided inert powder.

14 Claims, No Drawings

PENTAERYTHRITOL IN DRY DEVELOPERS

BACKGROUND OF THE INVENTION

1. Field of the Invention

This invention is in the field of non-destructive testing by means of the penetrant inspection process and is specifically directed to an improved dry developer composition for use in such process.

2. Description of the Prior Art

The penetrant method for detecting surface discontinuities or flaws has been extensively used for the inspection of wrought and cast products of both ferrous and non-ferrous metals, powder metallurgy parts, ceramics, plastics, and glass objects. In the typical penetrant inspection process, a liquid penetrant which may be oil based or water based is applied to the surface of the workpiece and allowed to penetrate into any flaws which extend to the surface. The penetrant composition may contain a flourescent pigment or a visible dye. After a sufficient dwell time, excess penetrant is removed from the surface by a remover, usually an emulsifier, which is compatible with the vehicle of the penetrant. The next step consists in applying a developer to the surface to assist in drawing out portions of the penetrant which have become lodged in surface flaws to render the same contrastingly visible to the background. An inspection is then made using either ultraviolet light in the case of a flourescent penetrant or ordinary white light in the case of a visible dye.

Both dry developers and developers consisting of suspensions in a fluid have been used in the penetrant inspection process. For any penetrant to be effective, it should have a combination of various physical properties. First, the developer must be absorptive toward the penetrant so as to maximize the blotting effect. It must have a fine grain size and a particle shape that will disperse and expose the penetrant at a flaw over as large a surface area as practical, while producing strong and sharply defined indications of flaws. The developer must be capable of effectively masking out interfering background colors and of providing a contrast background for indications, especially when color contrast penetrants are used. The developer must be easy to apply and it must form a thin uniform coating over a surface. The developer composition should be easily wetted by the penetrant at the flaw. In the case of fluorescent penetrants, the developer itself should be non-flourescent. It must be easy to remove after inspection and it must not contain ingredients harmful to parts being inspected or to equipment used in the inspection operation. Furthermore, it must not contain ingredients which are harmful or toxic to the operator.

Dry developers were the first developers to be used with fluorescent penetrants and are still widely used therewith. The first powders used were a simple mixture of chalk and talc which gave reasonably good results. As penetrant inspection became more widely used, however, these powders were no longer considered very practical. Instead, much lighter material such as amorphous silica powders were used which proved to be superior in many ways.

The ideal dry developer powders should be light and fluffy and should cling to dry metallic surfaces in a fine film. Adherence of the dry powder should not be excessive, however, because the amount of penetrant at fine flaws is so small that it cannot work through a thick coating of powder. The powder should not float and fill the air with dust.

Ideally, the dry developer powders should not be hygroscopic. If such powders pick up moisture when stored in areas of high humidity, they will lose their ability to flow and dust easily, and may pack or lump up in containers or in developer bins.

SUMMARY OF THE INVENTION

I have now found that very good results can be obtained in the penetrant inspection process by using a dry developer which consists of pentaerythritol alone or preferably in combination with one or more additional inert powders. I have found, for example, that such developers tend to have much lower levels of contamination with halide and sulfur bearing chemicals than do natural minerals such as talc. The compositions of the present invention also have a very low sodium content which is desirable in many instances. Specifically, I have found that the pentaerythritol should constitute at least 35% by weight of the dry developer composition, and should have a particle size such that at least 90% of the material is less than 20 microns in diameter. Particularly improved results are obtained when the pentaerythritol consists mostly of particles less than 10 microns in diameter.

In a preferred form of the invention, the finely divided pentaerythritol is combined with finely divided particles of an inert material having a lower bulk density than pentaerythritol. The bulk density of pentaerythritol is about 4.5 pounds per gallon (2.6 kg/l). For the purposes of the present invention, I prefer to combine this material with an inert material having a bulk density not in excess of about 2 pounds per gallon (1.16 kg/l).

DESCRIPTION OF THE PREFERRED EMBODIMENTS

The present invention provides a dry developer composition which is physically and chemically stable, and is transparent to the portion of the electromagnetic spectrum which includes the near ultraviolet and the visible so that it absorbs none of the incident radiation. While many materials meet these requirements, most if not all of those which contain mineral pigments also contain impurities such as sulfates, chlorides, or other halides, sodium, or potassium which make them unfit for use because one or more of these impurities left on the test piece after inspection can cause corrosion on metals and alloys at high temperatures. Sodium and halides cause corrosion of titanium, halides do so on stainless steel, and sulfur on nickel alloys. Natural pigments such as talc contain varying and unpredictable amounts of these elements.

The dry developers of the present invention containing substantial amounts of pentaerythritol meet the stringent requirements for dry developers. They are chemically inert toward objects in the inspection environment, they are relatively non-toxic, crystalline and friable.

The pentaerythritol particles can be used alone since they provide an excellent developer composition. However, the developer itself may be too dense to meet current military specifications, and is more dense than users are accustomed to.

The pentaerythritol, in the preferred form of the invention, is combined with finely divided particles of an inert material having a lower bulk density than that of the pentaerythritol. Typical inert materials include talc, magnesium carbonate, calcium carbonate, "Alon C" (which is a submicron hydrated aluminum oxide), silica aerogels of submicron particle size, "Tullanox 500" (which is a hydrophobic submicron fumed silica, low in sulfur and chlorine), and calcium silicate, in the form of natural woolastonite.

The following specific examples illustrate compositions of dry developers which can be used according to the present invention.

EXAMPLE I

100% pentaerythritol

EXAMPLE II

35–65% by weight pentaerythritol
Balance, talc.

EXAMPLE III

35–65% by weight pentaerythritol
Balance, magnesium carbonate.

EXAMPLE IV 35-65% by weight pentaerythritol
Balance, calcium carbonate.

EXAMPLE V

35–75% by weight of pentaerythritol
Balance, "Alon C".

EXAMPLE VI

35–75% by weight pentaerythritol
Balance, silica aerogels.

EXAMPLE VII

35–65% by weight pentaerythritol
Balance, "Tullanox 500".

EXAMPLE VIII

35–65% by weight pentaerythritol
Balance, calcium silicate (woolastonite).

EXAMPLE IX

50% by weight pentaerythritol
15% by weight "Tullanox 500"
35% by weight calcium silicate.

EXAMPLE X

50% by weight pentaerythritol
15% by weight "Tullanox 500"
35% by weight magnesium carbonate.

EXAMPLE XI

50% by weight pentaerythritol
15% by weight "Tullanox 500"
35% by weight calcium carbonate.

The calcium silicate used in the above formulations should be one which contains a low concentration of sulfur, sodium, and halogens. Fumed silicas are preferable to silica aerogels because they are less likely to contain contaminants. However, a high proportion of a pure pentaerythritol can permit the use of sulfur, chlorine or sodium bearing pigments by diluting these contaminants to an overall tolerable level.

The dry developers of the present invention are used in exactly the same manner as dry developers of the prior art. In other words, the penetrant is applied to the surface and the excess penetrant is removed, leaving entrapments of the penetrant in surface discontinuities or flaws. The dry developer powder is then dusted on or otherwise applied to the surface of the piece to act as a blotter for pulling up the penetrant indications by capillary action. The piece is then inspected under black light or white light depending on whether a fluorescent pigment or a visible dye was used in the penetrant.

It should be evident that various modifications can be made to the described embodiments without departing from the scope of the present invention.

I claim:

1. In the method of non-destructive testing for surface flaws in which a liquid penetrant is applied to the test surface, excess penetrant is removed while leaving penetrant entrapped in surface flaws and a dry developer powder is applied over the test surface to aid in drawing the entrapped penetrant to the surface and thereby render the location of said flaws visible, the improvement which comprises:
employing as said developer powder a dry composition including at least 35% by weight pentaerythritol powder at least 90% of said powder being less than 20 microns in diameter.

2. The method of claim 1 in which said developer contains finely divided particles of an inert material having a lower bulk density than pentaerythritol.

3. A method according to claim 2 in which:
said inert material has a bulk density not in excess of 2 lbs/gal (1.16 kg/l).

4. A method according to claim 1 in which:
said developer is a dry mixture of pentaerythritol and talc.

5. A method according to claim 1 in which:
said developer is a dry mixture of pentaerythritol and magnesium carbonate.

6. A method according to claim 1 in which:
said developer is a dry mixture of pentaerythritol and calcium carbonate.

7. A method according to claim 1 in which:
said developer is a dry mixture of pentaerythritol and a submicron particle size silica aerogel.

8. A method according to claim 1 in which:
said developer is a dry mixture of pentaerythritol and fumed silica.

9. A dry developer composition for use in the penetrant inspection method for locating surface flaws in a workpiece, said developer consisting essentially of a mixture of at least 35% by weight pentaerythritol having a particle size such that at least 90% of the particles are less than 20 microns in dimension and a finely divided inert powder with a bulk density lower than pentaerythritol.

10. A dry developer according to claim 9 in which:
said inert powder has a bulk density no greater than 2 lbs/gal (1.16 kg/l).

11. A dry developer according to claim 9 in which said inert powder is talc.

12. A dry developer according to claim 9 in which said inert powder is a submicron hydrated aluminum oxide.

13. A dry developer according to claim 9 in which said inert powder is a submicron silica aerogel.

14. A dry developer according to claim 9 in which said inert powder is a submicron fumed silica.

* * * * *